United States Patent
Lev

(10) Patent No.: US 11,357,715 B2
(45) Date of Patent: Jun. 14, 2022

(54) HAIR-COLORING COMPOSITION AND METHOD

(71) Applicant: Yael Lev, Vancouver (CA)

(72) Inventor: Yael Lev, Vancouver (CA)

(73) Assignee: Yael Lev, Vancouver (CA)

( * ) Notice: Subject to any disclaimer, the term of this patent is extended or adjusted under 35 U.S.C. 154(b) by 0 days.

(21) Appl. No.: 17/002,739

(22) Filed: Aug. 25, 2020

(65) Prior Publication Data
US 2020/0397679 A1    Dec. 24, 2020

Related U.S. Application Data

(63) Continuation of application No. PCT/CA2019/000028, filed on Feb. 27, 2019.
(Continued)

(51) Int. Cl.
*A61Q 5/10* (2006.01)
*A61K 8/41* (2006.01)
(Continued)

(52) U.S. Cl.
CPC ............. *A61K 8/41* (2013.01); *A45D 19/00* (2013.01); *A61K 8/19* (2013.01); *A61K 8/22* (2013.01);
(Continued)

(58) Field of Classification Search
CPC . A61Q 5/10; A61K 8/22; A61K 8/411; A61K 8/19; A61K 8/41; A61K 8/347;
(Continued)

(56) References Cited

U.S. PATENT DOCUMENTS

| 5,733,344 A | 3/1998 | Shiraishi et al. |
| 7,407,055 B2 | 8/2008 | Rodriguez |

(Continued)

FOREIGN PATENT DOCUMENTS

| CN | 2606380 | 11/2006 |
| JP | 10114635 | 5/1998 |

OTHER PUBLICATIONS

Mintel, Moroccan Ghassoul Facial & Body Mask Kit. Found at web page http://www.gnpd.com, Jul. 9, 2015.

*Primary Examiner* — Eisa B Elhilo
(74) *Attorney, Agent, or Firm* — Todd A. Rattray; Oyen Wiggs Green & Mutala LLP

(57) ABSTRACT

Hair dye composition and method of dyeing hair that targets only at least one grey part using a permanent hair dye component comprising a specific volume percentage of a particulate pigment to permanent hair dye component. The purpose of some embodiments of the invention is to delay the need for women to dye their hair in full. At least one pigment particle (about 0.0770 ml or about 1/64th of a teaspoon) may be added to a bottle of 71 ml of permanent hair dye, which allows the permanent hair dye composition to become visible and allows for more accuracy during application. Using small quantities of 5 cc per application (hair dye: 2.5 ml; developer: 2.5 ml) reduces the amount of dye applied to needless areas of the hair. The use of a make-up sponge stick allows for better accuracy. The composition is multi-use, and provides for 28 applications (71 ml bottle of dye and 71 ml of developer), and will save users time and money. All these characteristics provide for a hair dye composition that significantly reduces the amount of harmful chemicals applied to users' hair.

25 Claims, 3 Drawing Sheets

Related U.S. Application Data

(60) Provisional application No. 62/635,591, filed on Feb. 27, 2018.

(51) Int. Cl.

| | | |
|---|---|---|
| *A45D 19/00* | (2006.01) | |
| *A61K 8/19* | (2006.01) | |
| *A61K 8/22* | (2006.01) | |
| *A61K 8/34* | (2006.01) | |
| *A61K 8/49* | (2006.01) | |
| *A41D 19/00* | (2006.01) | |
| *A45D 19/06* | (2006.01) | |
| *A45D 7/00* | (2006.01) | |
| *G09B 19/00* | (2006.01) | |

(52) U.S. Cl.
CPC .............. *A61K 8/347* (2013.01); *A61K 8/411* (2013.01); *A61K 8/415* (2013.01); *A61K 8/4973* (2013.01); *A41D 19/0055* (2013.01); *A41D 2400/52* (2013.01); *A45D 19/0083* (2021.01); *A45D 19/06* (2013.01); *A45D 2007/001* (2013.01); *A45D 2200/25* (2013.01); *A61K 2800/412* (2013.01); *A61K 2800/4324* (2013.01); *A61K 2800/87* (2013.01); *A61K 2800/882* (2013.01); *G09B 19/00* (2013.01)

(58) Field of Classification Search
CPC ................. A61K 2800/43; A61K 8/415; A61K 2800/4324; A61K 2800/882; A45D 19/00; A45D 19/0083; A45D 19/0055; A45D 19/06; A45D 2007/001; A45D 2200/25
USPC .......................................................... 8/405
See application file for complete search history.

(56) References Cited

U.S. PATENT DOCUMENTS

| | | | |
|---|---|---|---|
| 7,682,402 B2* | 3/2010 | Kravtchenko | A61Q 5/08 8/111 |
| 2005/0193501 A1* | 9/2005 | Chan | A61Q 5/08 8/405 |
| 2006/0248660 A1* | 11/2006 | Ryan | A61K 8/44 8/405 |
| 2006/0248663 A1* | 11/2006 | Tremblay | A61K 8/27 8/405 |
| 2007/0044249 A1* | 3/2007 | Lisowski | A45D 19/012 8/405 |
| 2009/0031505 A1 | 2/2009 | Kravtchenko et al. | |
| 2017/0266086 A1* | 9/2017 | Lechner | A61K 8/922 |

* cited by examiner

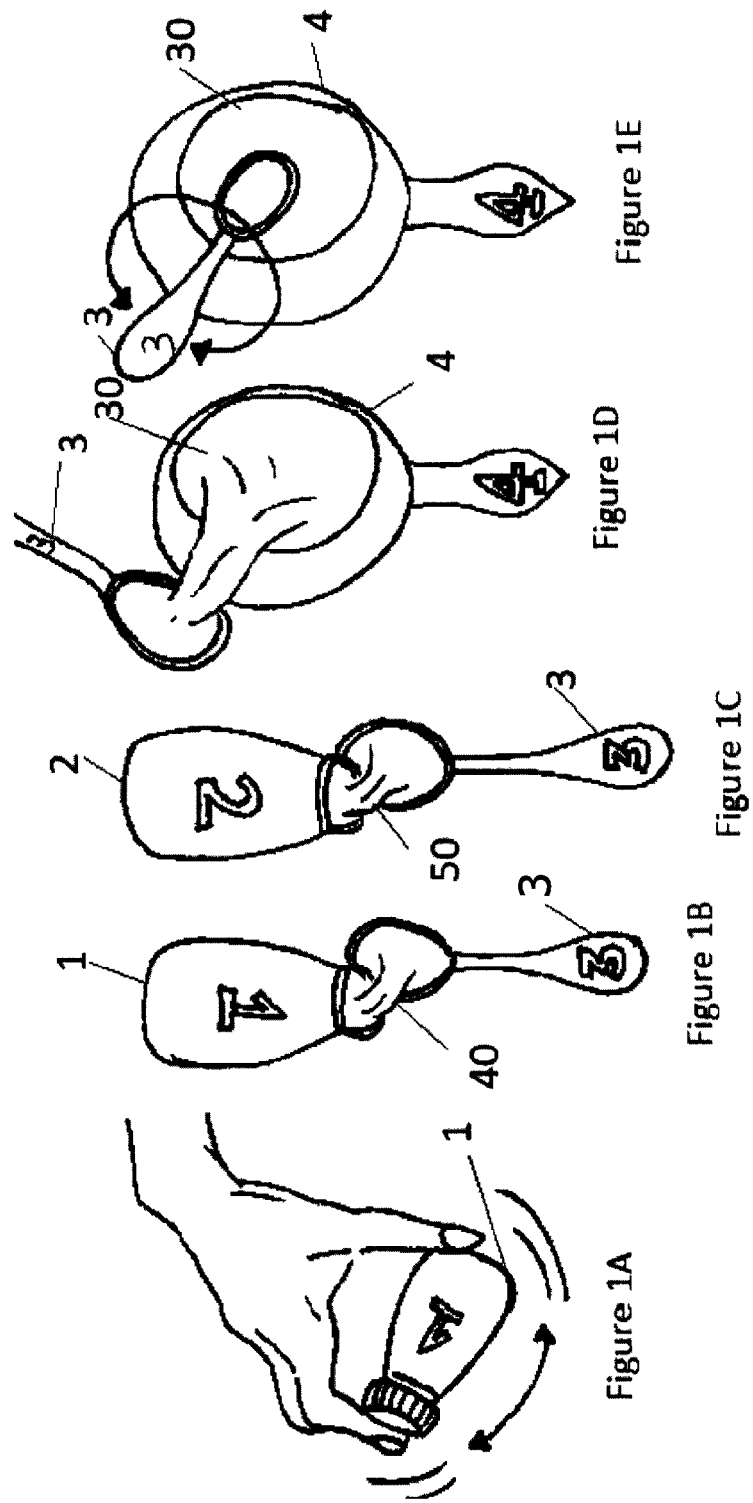

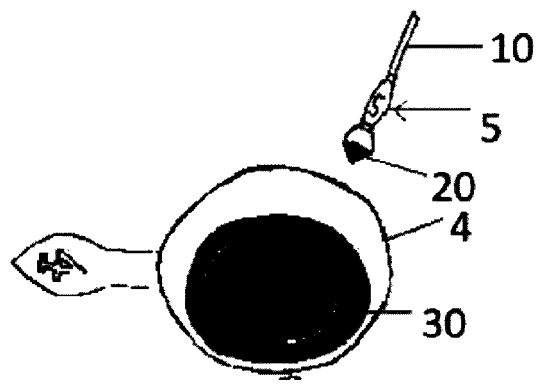
Figure 1F
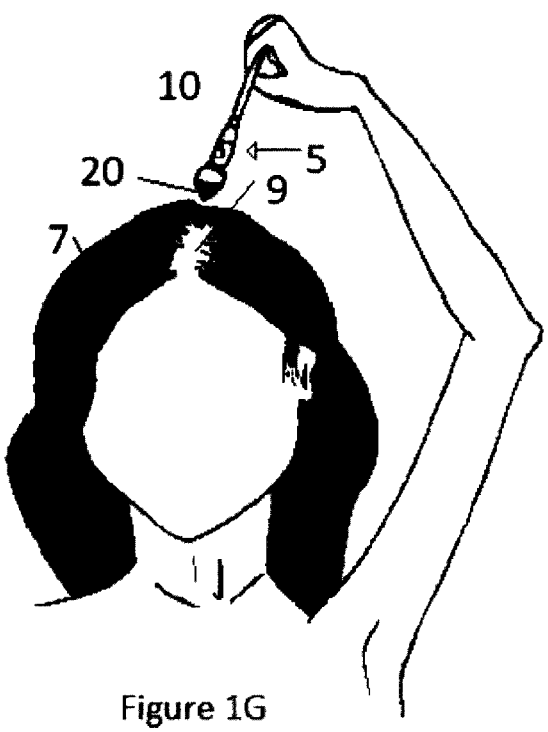
Figure 1G
Figure 1 (cont'd)

HAIR-COLORING COMPOSITION AND METHOD

CROSS-REFERENCE TO RELATED APPLICATIONS

This application is a continuation of application Patent Cooperation Treaty application No. PCT/CA2019/000028 having an international filing date of 27 Feb. 2019 which in turn claims priority to, and the benefit under 35 U.S.C. § 119 of, application No. 62/635,591, filed 27 Feb. 2018. All of the applications referred to in this paragraph are hereby incorporated herein by reference.

FIELD OF THE INVENTION

The invention, in some embodiments, relates to the field of hair-coloring, and more particularly but not exclusively, to methods and compositions suitable for coloring hair, especially human hair.

BACKGROUND OF THE INVENTION

There is often a need for coloring human hair. One particular need is to color natural grey hair that grows, for example, in older people. Current methods and compositions for coloring such natural grey color have disadvantages.

The continuous and rapid growth of the visible grey roots is one of the major esthetic problems for women worldwide. This unsolved issue is the main reason women are forced to dye their entire hair on a regular basis. This cycle of continuous dyeing of the hair for years poses a major health risk and can permanently damage the hair. This process is time consuming, expensive, and involves dangerous chemicals that can damage the hair. The many applications over the years, often until old age, are harmful and dangerous to the hair. The chemicals can harm the skin, breathing airways and the hair itself.

Even with the knowledge of the risks involved with permanent hair dye, women continue to buy and dye their hair on a regular basis because permanent hair dye produces the best results compared to other types of hair dye, and permanent hair dye lasts longer on the grey roots. The following application of permanent hair dye is only necessary once the grey roots grow back from the scalp.

Permanent hair dye compositions in the market today do not have their final color when applied and thus the users have no control over the application and are forced to dye significantly more than necessary. It takes about 1-3 minutes after the permanent hair dye composition has been applied to hair for any color to show, and it only becomes fully clear after washing. Before the application, the permanent hair dye composition appears like shampoo with an unclear color shade, and during the application it is difficult to determine what gets dyed and what doesn't. This causes the user to apply the permanent hair dye compositions to unnecessary locations on the hair which results in too much dye on the hair and leads to dripping on the neck, forehead and side burns.

All the liquid permanent hair dye compositions on the market appear dark/light orange or dark/light yellow. For example, black liquid permanent hair dye appears to be orange and red hair dye also appears to be orange; the same goes for the rest of the colors. All the cream permanent hair dye compositions on the market either appear white or other colors that do not match the wanted color of the finished hair dye product. The quantity of hair dye composition sold are too great and cause the users to apply unnecessary amounts of hair dye composition to the hair. During the mixing process of the hair dye and the developer, and due to the great quantities used, a strong and uncomfortable chemical scent is evident, and can sometimes cause difficulties in breathing when used.

The permanent hair dyes on the market today are all intended for single use. Due to the large quantity available, the user is then forced to either throw away a large quantity of hair dye or use it unnecessarily on the hair.

Due to rapid hair growth and the emergence of grey roots in women's hair, they are forced to dye their hair every two to four weeks.

Following the application process, users are always forced to wash their hair thoroughly, a process that takes time and is inconvenient.

There are commercially-available hair brushes for applying permanent hair dye compositions to the hair. The permanent hair dye brushes in the market are all very similar and are of the same style. Some of the brushes are double sided, with one side being used as a stick to split the hair and reach the roots. The other side has the brush hair bristles and sometimes includes a comb as well. Other brushes vary in size, shape and form. Some are made of plastic, and some from silicone. Some of the brush bristles also vary in composition, as some are tighter together and others looser.

Currently available permanent hair-coloring compositions typically include para-phenylenediamine (PPD), hydrogen peroxide, ammonia, paraben preservatives, lead acetate and resorcinol. PPD is used as a dye for dark color shades and is made from coal tar, a petroleum-derived chemical that includes benzene, naphthalene, phenols, aniline, and other chemicals. PPD is also used as a wood preservative, and contact with skin is best to be avoided. Research states PPD in combination with hydrogen peroxide is very toxic and can lead to cancer.

Hydrogen peroxide is mostly used to strip the natural color away, before applying the hair dye color composition. It is said to change the hair structure and make it brittle, stripping it of its natural luster.

Ammonia is used to open up the hair's cuticle (the outer layer of the hair) so the dyes can come into the shaft (the inside of the hair). It may produce caustic burns and lung irritation.

The two most common parabens preservatives are Methylparabens and Propylparabens. They are widely used in hair care products and can produce severe allergies and skin irritation.

Lead Acetate is used as a coloring additive for the dark shade hair dyes. It is said to cause anemia and produce neurological problems.

Resorcinol is a toxic dye that can cause scalp irritation, and is an allergen affecting the endocrine system.

There are many companies that produce permanent hair dye compositions in the market today. Some of the companies are well known and others not very known. Permanent hair dye compositions are sold in kits or tubes of permanent hair dye or developer (separately). After properly applied, the dyeing of hair caused by permanent hair dye compositions does not come off the hair during or after washing the hair. Permanent hair dye compositions do not have their final color during application. This in fact means that the wanted color does not show during application, only 1-2 minutes after application.

Permanent hair dye products in the market today are for single use only.

Some of the better-known companies in the market today and the quantities of permanent hair dye compositions they sell are listed below.

L'Oreal™ produces a kit including two components, 71 ml dye and 71 ml developer that when mixed provide 142 ml of permanent hair dye composition. Garnier™ produces a kit including two components, 60 ml dye and 60 ml developer that when mixed provide 120 ml of permanent hair dye composition.

Clairol™ Nice easy is a kit including two components, 25 ml dye and 15 ml developer that when mixed provides 40 ml of permanent hair dye composition.

Schwarzkopf™ that produces a kit including two components, 50 ml dye and 50 ml developer that when mixed provides 100 ml of permanent hair dye composition.

Indola produces a kit including two components, 60 ml dye and 60 ml developer that when mixed provide 120 ml of permanent hair dye composition.

Revlon™ produces a kit including two components, 60 ml dye and 60 ml developer that when mixed provide 120 ml of permanent hair dye composition.

Wella™ produces a kit including two components, 40 ml dye and 40 ml developer that when mixed provide 120 ml of permanent hair dye composition.

The above are just a few examples of quantities of hair dye and developer that are present in the permanent hair dye kits and tubes in the market today.

There are also some temporary products in the market for the purpose of covering up the visible grey roots. These products try to solve the problem of the rapid growth of the grey roots. These products exist to try and delay dyeing the entire hair for as long as possible. These products are temporary and come off the hair after washing. These products are for multi-uses, unlike permanent hair dye products. These temporary products come with cosmetic pigment meaning that as soon as the dye is applied to the hair the wanted color is visible. These temporary products fade throughout the day and come off the hair complete after washing with water. Examples of such products include: MAGIC RETOUCH™-spray" by L'Oreal, Cover your Grey™ Touch up stick light, ASH™ Infinity Touch-Up™ Hair color mascara and ColorMark Grey™ roots gone instantly.

There are many similar products in the market today. All these products have the same common feature, the hair dye comes off the hair after washing.

It would be useful to have methods and devices for effectively coloring hair quickly and permanently that have one or more advantages compared to known methods and compositions.

SUMMARY OF THE INVENTION

According to one aspect, the disclosure herein is addressed to a hair dye composition comprising a predetermined amount of a permanent hair dye component of a type that is mixed with a predetermined developer component in a predetermined ratio by volume to prepare a permanent hair dye composition that is applied to a subject's hair and maintained in the subject's hair for at least a period of a predetermined minimum duration before washing the subject's hair, the permanent dye component comprising one or more compounds, for example at least one compound or a set of compounds that determines the color of the subject's hair after washing, the one or more compounds, for example, at least one coupler compound, present in an amount effective to attain a selected hair color of the subject's hair, the selected color arranged to match a predetermined color selected by or for the subject such that the permanent hair dye composition may be used to touch-up at least one grey part of the subject's hair in new growth areas to match at least one non-grey part previously dyed to attain the predetermined color, the permanent hair dye component comprising from about 0.05% to about 0.11% by volume of at least one pigment particle, optionally a plurality of pigment particles, that is evenly distributable within the permanent hair dye composition, the at least one pigment particle being of a visible color such that application of the permanent hair dye composition to a surface of the at least one grey part of the subject's hair may be observed to have the visible color of a plurality of the at least one pigment particle contemporaneously with application to the surface (for example, to determine at least one grey part or area to which the permanent hair dye composition has already been applied).

In another aspect, the disclosure is addressed to a method for touching up a grey new growth area of a subject's hair having a non-grey part dyed with a permanent dye of a predetermined color, the method comprising the following steps carried out by or for the subject: a) shaking a permanent dye component, optionally in a predetermined manner; b) mixing the permanent dye component with a predetermined developer component in a predetermined ratio by volume to prepare a permanent hair dye composition comprising at least one compound or a set of compounds that determines the color of the subject's hair after washing, the at least one compound or set of compounds, for example, at least one coupler compound, present in an amount effective to attain a selected hair color of the subject's hair that matches the predetermined color;

c) applying the permanent hair dye composition to at least one grey part, preferably grey parts, of the subject's hair;

d) allowing the permanent hair dye composition to remain in the subject's hair for at least a period of predetermined minimum duration; and e) washing the permanent hair dye composition out of the subject's hair.

Wherein the permanent hair dye component comprising 0.05% to about 0.11% by volume of at least one pigment particle of a visible color such that application of the permanent hair dye composition to a surface of the grey part of the subject's hair may be observed to have the visible color of a plurality of the at least one pigment particle contemporaneously with application to the surface, the predetermined manner sufficient to suspend and preferably evenly disperse the at least one pigment particle in the permanent hair dye component.

In one aspect, the disclosure is addressed to making a hair dye composition comprising the step of mixing a predetermined quantity of at least one pigment particle (in a dry or suspended form) into a predetermined volume of a permanent hair dye component in a ratio of 0.05% to about 0.11% volume (or an equivalent ratio by weight or weight/volume).

In one aspect, the disclosure is addressed to making a hair dye composition comprising the step of adding a predetermined quantity of at least one pigment particle (in a dry or suspended form) into a predetermined volume of at least one component of a permanent hair dye component to form an additive and mixing the additive with at least one other component of permanent hair dye component such that the at least one pigment particle is present in the permanent hair dye component is in a ratio of from about 0.05% to about 0.11% volume (or an equivalent ratio by weight or weight/volume).

According to one embodiment, the disclosure herein is addressed to hair dye composition comprising a predetermined amount of a permanent hair dye component of a type that is mixed with a predetermined developer component in a predetermined ratio by volume to prepare a permanent hair dye composition that is applied to a subject's hair and maintained in the subject's hair for at least a period of a predetermined minimum duration before washing the subject's hair, the permanent dye component comprising at least one coupler compound and at least one primary intermediate compound, the at least one coupler compound and the at least one primary intermediate compound present in effective amounts to attain a selected hair color of the subject's hair, the selected color arranged to match a predetermined color selected by or for the subject such that the permanent hair dye composition may be used to touch-up at least one grey part of the subject's hair in new growth areas to match at least one non-grey part previously dyed to attain the predetermined color, the permanent hair dye component comprising 0.05% to about 0.11% by volume of at least one pigment particle that is evenly distributable within the permanent hair dye composition, the at least one pigment particle being of a visible color such that application of the permanent hair dye composition to a surface of the at least one grey part of the subject's hair may be observed to have the visible color of a plurality of the at least one pigment particle contemporaneously with application to the surface.

Referring to both the hair dye composition and the method aspects:

In one embodiment, the permanent dye component comprises from about 0.09% to about 0.11% by volume of the at least one pigment particle.

In one embodiment, the percentage by volume of the at least one pigment particle in the permanent dye component does not exceed about 0.11%, with the proviso that when the selected color is black the percentage by volume does not exceed about 0.10%.

In one embodiment, the percentage by volume of the at least one pigment particle in the permanent dye component is about 0.11%.

In one embodiment, the permanent hair dye component comprises a primary intermediate compound, optionally in tile form of an aromatic amine that forms an imine on oxidation, the aromatic amine optionally being selected from the group consisting of 1,4-diaminobenzene, diaminotoluene, p-aminophenol and combinations thereof, a hair-cuticle opening agent optionally selected horn the group consisting of ammonia, ethanolamine, diethanolamine, sodium carbonate and combinations thereof, and at least one coupler compound optionally selected from the group consisting of a phenol, naphthol, resorcinol, 4-chlororesorcinol, benzodioxole, 1,4-diaminobenzene, 2,5-diaminotoluene, p-aminophenol, derivatives thereof and combinations thereof.

In one embodiment, the predetermined developer component comprises an oxidizing agent, for example, hydrogen peroxide.

In one embodiment, the visible color of the at least one pigment particle matches the predetermined color.

In one embodiment, the particle size of 99% by weight of the at least one pigment particle does not exceed 150 microns.

In one embodiment, the particle size of at least 99% by weight of the at least one pigment particle is between 10 and 100 microns.

In one embodiment, the permanent hair dye component is contained in a container, the container comprising a reusable closure device and a predetermined volume of the permanent hair dye component in a liquid form, the predetermined volume being sufficient for multiple touch-up applications of the hair dye composition to new growth (i.e. areas that are grey) of a non-grey part of the subject's hair of the predetermined color.

In one embodiment, the permanent hair dye component is contained in a container, the container comprising a reusable closure device and a predetermined volume of the permanent hair dye component in a cream form, the predetermined volume sufficient for multiple touch-up applications of the hair dye composition to new growth (i.e. areas that are grey) of a non-grey part of the subject's hair of the predetermined color.

In one embodiment, die container is provided with instructions in at least one language for shaking the container (when in liquid form) before use to suspend the at least one pigment particle in the permanent hair dye component and mixing a specific volume of the predetermined amount of the permanent hair dye component with a predetermined amount of the predetermined developer component corresponding to the predetermined ratio by volume.

In one embodiment, the specific volume corresponds to a defined period of new growth (of grey hair e.g. a suggested range of time expressed in days and/or weeks) from a previous application of a permanent hair dye composition of the predetermined color that covered at least the roots of the subject's hair, the partial volume identified in the instructions as a recommended amount for a single application to the at least one grey part of the subject's hair for the defined period of new growth.

In one embodiment, the defined period of new growth is 2 to 3 weeks and the partial volume is approximately 2.5 milliliters.

In one aspect, the disclosure is addressed to a kit.

In one embodiment, the kit comprises a hair dye composition described above in any one or more embodiments in any combination.

In one embodiment, the kit further comprises a second container with a reusable closure, the second container comprising at least a volume of the predetermined developer component sufficient to make the permanent hair dye composition in an amount sufficient for a selected number of applications.

In one embodiment, the kit further comprises an applicator, the applicator comprising at least one surface with a surface area configured for selectively applying the permanent hair dye composition to an area of subject's hair, said area substantially comprising a grey part of the subject's hair including an area proximal to the roots of the subject's hair.

In one embodiment, the at least one surface is a flat edge or pointed tip.

In one embodiment, the applicator is a washable sponge applicator.

In one embodiment, the instructions further comprise instructions for using the kit including applying the permanent hair dye composition to the subject's hair with a suitable applicator, allowing the permanent hair dye composition to remain in subject's hair for at least the period and washing the hair after this period.

In one embodiment, the kit further comprises a mixing bowl of a volume sufficient to mix an amount of the permanent hair dye component at least sufficient for one application with an amount of developer in the predetermined ratio by volume.

In one embodiment the kit further comprises gloves.

In one embodiment, the kit further comprises a measuring spoon, optionally a measuring spoon suitable for measuring a volume of approximately 2.5 milliliters.

In another aspect, the disclosure is addressed to a kit comprising at least a container containing a predetermined amount of a permanent hair dye component and a container containing a predetermined amount of the at least one pigment particle or a suspension thereof. Optionally, the respective predetermined amounts correspond to a ratio of from about 0.05 to about 0.11% by volume of the at least one pigment particle in the permanent hair dye component (e.g. about 0.11% by volume). Optionally, the kit is provided with a measuring or dispensing device for adding a precise quantity of the at least one pigment particle or a suspension of the at least one pigment particle (e.g. in a certain ratio by volume) to a predetermined quantity of the permanent hair dye component such the permanent hair dye component contains 0.05 to about 0.11% by volume of the at least one pigment particle (e.g. about 0.11% by volume). Optionally the kit is provided with instructions for mixing the at least pigment particle into the permanent hair dye component to achieve the intended ratio by volume. The kit optionally comprises one or more of the aforementioned kit components (third container containing a developer component, applicator etc.) in any combination.

BRIEF DESCRIPTION OF THE FIGURES

FIG. 1 consists of FIGS. 1A-1G which describe respective steps of one embodiment of a method described herein including a method of touching up a grey new growth area of a subject's hair, a method of using a hair dye composition described herein and a kit comprising a hair dye composition described herein.

FIG. 1A depicts one embodiment of a step of shaking a bottle of the permanent hair dye component to suspend the pigment particles such that the permanent hair dye component when poured in a desired amount into a measuring spoon will have a quantity of pigment particles that allow the pigment particles to be visible when mixed with the predetermined developer component and applied to the subject's hair; optionally as a result of shaking the pigment particles will be substantially uniformly distributed within the permanent hair dye component;

FIG. 1B depicts a step of pouring the permanent hair dye component into the measuring spoon;

FIG. 1C depicts a step of pouring the predetermined developer component into the measuring spoon;

FIG. 1D depicts a step of pouring the contents of the measuring spoon into the mixing bowl such that the mixing bowl contains the permanent hair dye component and the predetermined developer component;

FIG. 1E depicts a step of mixing the permanent hair dye component and the predetermined developer component to form a permanent hairy dye composition.

FIG. 1F depicts a step of dipping an applicator into the mixing bowl, a step repeated as desired.

FIG. 1G depicts a step of using an applicator to apply the permanent hair dye composition to the gray parts of the subject's hair, for example gray new growth areas emerging from the hair roots; a step repeated as desired.

DETAILED DESCRIPTION

Figure 2:
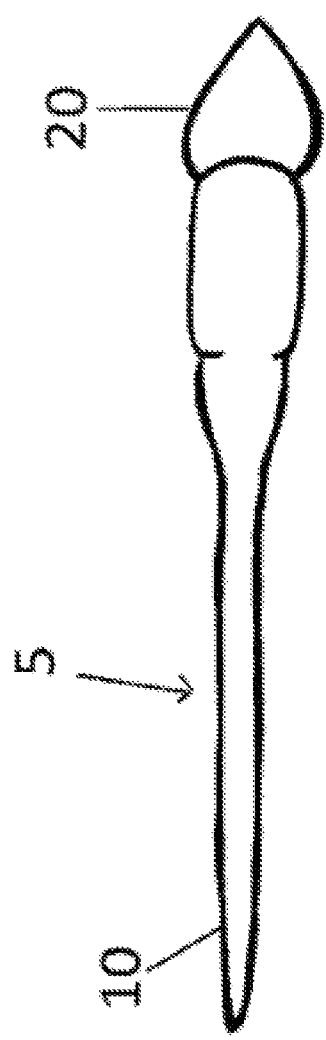
FIG. 2 depicts one embodiment of an applicator for use in accordance with steps depicted in FIGS. 1F and 1G.

Some embodiments of the invention are herein described with reference to the accompanying figures. The description, together with the figures, makes apparent to a person having ordinary skill in the art how some embodiments of the invention may be practiced. The figures are for the purpose of illustrative discussion and no attempt is made to show structural details of an embodiment in more detail than is necessary for a fundamental understanding of the invention. For the sake of clarity, some objects depicted in the figures are not to scale.

In the Figures:

FIG. 1 is a set of FIGS. 1A-1G depicting steps in one embodiment of a method as follows:

As seen in FIG. 1A, according to one embodiment of a method herein, a container in the form of a bottle 1, containing the permanent hair dye component, is shaken to suspend the at least one pigment particle;

As seen in FIG. 1B, according to one embodiment of a method herein, a specific volume of approximately 2.5 ml of the permanent hair dye component 40 is poured from the bottle I containing the permanent hair dye component 40 into a measuring spoon 3; depending on the volume amounts (e.g. whether or not two 2.5 ml. amounts can be measured individually with one 5 ml. spoon) measurable by the spoon measuring spoon contents are optionally first poured into the mixing bowl 4 before step 1C;

As seen in FIG. 1C, according to one embodiment of a method herein, a specific volume of approximately 2.5 ml of the predetermined developer component 50 is poured from the second container containing the predetermined developer component 50, optionally in the form of bottle 2, into the measuring spoon 3;

As seen in FIG. 1D, according to one embodiment of a method herein, a specific volume of the permanent hair dye component 40 and a specific volume of the developer component 50 50 are added to mixing bowl 4.

As seen in FIG. 1E, according to one embodiment of a method herein, the contents of mixing bowl 4 are mixed to form a permanent hairy dye composition 30 having a resulting volume of 5 ml, optionally using the measuring spoon 3.

As seen in FIG. 1F, according to one embodiment of a method herein, the tip 20 of an applicator in the form of the make-up sponge stick 5 is gently dipped into the permanent hair dye composition (color-visible) in mixing bowl 4; and As seen in FIG. 1G, according to one embodiment of a method herein, the permanent hair dye composition 30 is then applied using the applicator 5 to the-visible grey hair with small gentle bursts, so that the permanent hair dye composition 30 will penetrate at least at one grey part 9 of the subject's hair 7 to which it was applied approximately 30 minutes after the application, whereupon the hair is preferably washed (not shown).

As seen in FIG. 2, according to one embodiment, the applicator is in the form a sponge applicator 5 having a handle 10 and a pointed tip 20 for ease of application to a least one grey part of the subject's hair.

It will be understood that a defined % by volume can most often be expressed in amounts by weight or as ratio of weight to volume or volume to weight and the disclosure shall be understood to include all substantially equivalent ways of expressing relative amounts in general or with reference to a specific pigment particle, hair dye composition, permanent hair dye composition 30 or permanent hair dye component 40.

It will be understood that the step of mixing a component, composition or substance may be carried in a variety of ways that result in making a new composition with the intended relative quantities of respective amounts added to one another.

The term "about" means with reference to a quantity expressed with a specificity of 3 decimal places plus/minus 0.0005, and with a specificity of two decimal places, plus/minus 0.005 and with reference to a quantity expressed with one decimal place, plus/minus 0.05.

At the time of this writing, the most common permanent hair coloring methods are based on quinone imine dyes, the methods herein optionally implemented using a kit, generally referred to in the description of embodiments below (describing the same item) as a hair-coloring kit, that includes two components, a permanent hair dye component 40, generally referred to in the description of embodiments below (describing the same item) as a coloring solution, dye precursor or color precursor and a predetermined developer component 50, generally referred to in the description of embodiments below (describing the same item) as a developer 50.

The term pigment particle may be variously referred to in the description of embodiments below. These terms, for example, particulate pigment and cosmetic particulate pigment, denote the same item. References to cosmetic pigment shall be understood to refer to pigment particles that lend their color to the permanent hair dye composition 30 upon application to delineate parts of hair (areas) to which a permanent hair dye composition 30 was just applied to facilitate progressing coverage of areas in need of application. Some of these may be used in the cosmetics industry but use of the term"cosmetic" is a more general way of referring to a surface property, of lending surface color.

In one embodiment, the coloring solution i.e. permanent hair dye component 40, is an aqueous solution that includes ammonia (present as ammonium hydroxide due to the inherent reaction of ammonia with water) and dye precursors (an aromatic amine"primary" and a coupler compound that is also referred to in the description of embodiments below as a coupler or coupling agent, referring to the same item). The term hair-coloring composition or hair coloring solution may be used to refer the hair dye composition claimed herein.

In some embodiments of the disclosure is addressed to methods and compositions suitable for coloring hair, especially human hair.

The principles, uses and implementations of the teachings of the subject matter herein may be better understood with reference to the accompanying description and examples. Upon perusal of the description and examples present herein, one skilled in die art is able to implement the teachings herein without undue effort or experimentation.

Before explaining at least one embodiment of a method, composition or kit in detail, it is to be understood that the disclosure of method, composition or kit is not necessarily limited in its application to the details of construction and the arrangement of the components and/or methods set forth herein. The method, composition or kit is amenable to other embodiments or of being practiced or carried out in various ways. The phraseology and terminology employed herein are for descriptive purpose and should not be regarded as limiting.

The developer 50 as optionally used in FIG. 1C is usually an aqueous solution including 6% hydrogen peroxide as an oxidant.

For use, the two components are mixed to form a hair-coloring composition that is basic due to the presence of the ammonia and, in some instances, additional basifying agents.

The hair-coloring composition is applied to the hair as exemplified in FIG. 1F and allowed to be in contact with the hair for a period of time, the period of time varying between 25 to 40 minutes (varies amongst product).

During the period of time, the ammonia opens the cuticle layer of the hairs, allowing the dye precursors and ox-idant to penetrate into the hair cortex. Inside the cortex the dye precursors react with the oxidant under basic conditions:

the primary is oxidized by the oxidant yielding a reactive aromatic imine;

the reactive aromatic imine reacts with the coupler through electrophilic aromatic substitution yielding an intermediate; and the intermediate oxidizes to give the final dye that colors the hair.

In parallel, both the ammonia and the oxidant bleach the natural hair colorants (melanin and eumelanin) so that the color provided by the final dye is more apparent.

After the period of time, the hair is rinsed with water, thereby removing hair-coloring composition remaining outside the hair and removing the ammonia so that the cuticle layer closes. The final dye molecules have a relatively high molecular weight so are trapped inside the hair cortex and do not readily leach from the hair.

The final color of the dye molecules is dependent on the exact nature of the primary and the coupler. The color of the hair that is dyed is dependent on the color of the dye molecules, the original hair color, the concentration of oxidant in the composition and the time the composition is in contact with the hair.

Typically, the primary is an aromatic amine that forms an imine on oxidation such as 1,4-diaminobenzene (paraphenylenediamine, PPD), diaminotoluenes and p-aminophenols.

Typical couplers include compounds identical to the primary, phenols, naphthols, resorcinol, 4-chlororesorcmol, benzodioxoles. and derivatives thereof.

For instance, a commercially available kit marketed as 4/77 (velvety brown) Koleston by Wella includes in the coloring solution:

water, ammonium hydroxide, toluene-2,5-diamine sulfate, resorcinol, 2-amino-6-chloro-4-nitrophenol and in the developer 50 (FIG. 1C):

water, hydrogen peroxide and other ingredients to increase viscosity.

An important use of permanent hair coloring such as discussed above is to dye grey hair, for example, grey hair that naturally occurs in older humans. The method of application as described above means that the entire length of all of the hair is in contact with the hair-coloring composition every time the hair is colored, typically once a month. This repeated contact with ammonia and hydrogen peroxide permanently damages the hair, so that the hair appears irremediably ratty, especially further from the scalp.

Some embodiments to which the disclosure is addressed herein relate to compositions, kits and methods suitable for coloring hair, especially human hair, that may have one or more advantages compared to known compositions, kits and methods.

Specifically, some embodiments relate to a hair-coloring composition that is easily applicable only to the portions of hair that need to be colored (e.g., the grey-colored portions near the scalp) as well as methods for applying the composition. It has been found that by implementing the teachings herein, hair is quickly, evenly and effectively colored with little mess.

A composition according to the teachings herein comprises a suspended particulate pigment. Some embodiments of a composition according to the teachings herein may be considered similar, substantially identical to or identical to known permanent hair-coloring compositions with the addition of particulate pigment.

The particulate pigment in the composition allows the user to see the chosen color of the composition prior to application, for example, while the composition is in the bottle or the tubes.

During application, the user can see the color being applied to the hair directly and thus can apply the dye with much more accuracy. This reduces the amount of dangerous chemicals that are applied to the user's hair as well as reduces the time and mess it takes to apply current prior art compositions that are colorless.

The ability to use a composition according to the teachings herein multiple times using small quantities only on the visible grey roots. For example, 80 ml of composition allows 16 applications (each application being about 5 ml). Using small quantities delays the need to fully dye the hair and reduces the amount of harmful chemicals that are applied to the hair. This may save users time and money. Using small quantities per application and the addition of cosmetic pigment substantially eliminates the chemical scent associated with hair coloring. Current commercially-available permanent hair dye kits are single-application only.

Preferably, an applicator, for example, as seen in the figures (1F, 1G, 2) in the form of make-up sponge stick 5 is used to apply to permanent hair dye composition 30 according to the teachings herein to the at least one grey part 9 in the form of visible grey roots. A pointed tip 20 on the sponge stick 5 enables the user to apply the permanent hair dye composition 30 more accurately to specific small spots of visible grey. This again saves time and money and reduces the amount of chemicals.

Chemistry of Permanent Hair Coloring

Permanent hair coloring requires three components: (1) a primary intermediate agent, (2) a coupling agent, and (3) an oxidant. The process is typically performed under basic conditions.

The mechanism of oxidation dyes involves three steps:
1—Oxidation of the primary intermediate;
2—Reaction of this with a coupler compound; and
3—Oxidation of the resulting compound to give the final dye.

The preparation (dye precursors) is in the leuco (colorless) form. Oxidizing agents are usually hydrogen peroxide, and the alkaline environment is usually provided by ammonia. The combination of hydrogen peroxide and ammonia causes the natural hair to be lightened, providing a "blank canvas" for the dye. Ammonia opens the hair shaft pores so that the dye can actually diffuse inside the fiber. These dye intermediates and coupler compounds can undergo oxidation and coupling reaction to form high molecular weight products, which are trapped in the hair matrix and cannot be readily removed through washing.

In the present invention, the composition, by including a cosmetic pigment powder, takes on the desired final color of the hair to be treated before the composition is applied to the hair.

The kit, components of which are diagrammatically depicted in FIGS. 1A to 1G, by which the product is provided to the consumer has the dye precursor and the cosmetic pigment premixed in one bottle.

Composition According to the Teachings Herein

Thus, according to an aspect of some embodiments of the teachings herein there is provided a composition suitable for coloring hair comprising:

a. liquid/cream permanent hair dye component 40 (FIG. 1B) with cosmetics particulate pigment included therein; and b. cream developer 50 or oxidant (hydrogen peroxide) (FIG. 1C).

The color of the cosmetics particulate pigment is of any suitable color, especially black, shades of brown, shades of red, oranges, blues and greens.

A general definition of a pigment could mean any substance that alters the color of a material through selective color absorption.

Types of Particulate Pigments

The cosmetic particulate pigment used herein may be any suitable water-insoluble pigment that is present as solid particles, for example, particulate pigments known in the art of cosmetics.

Examples of suitable cosmetic particulate pigments include those listed above.

In preferred embodiments, in the composition there are substantially no pigment particles larger than 150 micrometers, e.g. less than 1% by weight of all pigment particles in the composition are larger than 150 micrometers.

Cosmetic pigment particles are added to both liquid-form permanent hair dye component 40 and to creme-form permanent hair dye component 40 (FIGS. 1B and 1C).

The amount added is about 0.0770 ml or about 1/64 tsp (US measurements) of cosmetic pigment to a bottle of 71 cc of liquid (or creme) permanent hair dye.

Any ratio substantially less than the above-specified quantity has been determined to result in a successful application (FIG. 1G) of permanent hair dye composition 30 (the color does not wash out when the subject rinses the composition out of the subject's hair), but for certain colors, the color of the at least one pigment particle might not be visible in the permanent hair dye composition 30, thus making accurate coloring more difficult.

Any more than the above-specified quantity can interfere with the penetration or retention of the permanent hair dye composition 30 thus resulting in the dye coming off or out of the hair, for example, even completely, during washing.

Hair-Cuticle Opening Agent

The hair-cuticle opening agent is any suitable hair-cuticle opening agent for example, hair-cuticle opening agents known in the art. In some embodiments, the hair-cuticle opening agent is selected from the group of ammonia, ethanolamine, diethanolamine, sodium carbonate and combinations thereof. As is known to a person having ordinary skill in the art, some such agents are present in solution in an equivalent form, for example, ammonia is typically present in the composition as NH4+OH—.

Dye Precursor

The dye precursor is any suitable dye precursor as known in the art of permanent hair coloring compositions and described above, typically comprising an aromatic amine "primary" and a coupler.

In some embodiments, the primary is an aromatic amine that forms an imine on oxidation. In some such embodiments, the primary is selected from the group consisting of 1,4-diaminobenzene (paraphenylenediamine, PPD), 2,5-diaminotoluenes, p-aminophenols and combinations thereof.

In some embodiments, a coupler is identical to the primary. In some embodiments, the coupler is selected from the group consisting of phenols, naphthols, resorcinol, 4-chlororesorcinol, benzodioxoles, 1,4-diaminobenzene, 2,5-diaminotoluenes, p-aminophenols derivatives thereof and combinations thereof.

Oxidant

The oxidant is any suitable oxidant effective in causing the formation of a dye from the dye precursor by initiating the reaction of the primary with the coupler. Any suitable oxidant may be used, especially oxidants known in the art of hair-coloring compositions. In some embodiments, the oxidant is hydrogen peroxide. Oxidation takes place when an unstable atom loses an electron, thus allowing the atom to form a new compound with another element. In the context of coloring hair, the oxidizing agent hydrogen peroxide is typically used. When hydrogen peroxide is combined with a para-dye an 'imine' structure develops, creating a new compound called a meta-dye. During the application stage, para-toluene-diamine (PTD), a small salt crystal is dissolved in the tinting cream. The alkali within the mix helps to soften the hair, opening up the cuticle layer and allowing the PTD dyestuff to enter the cortex. Para-dyes are oxidized and polymerization occurs, PTD para-dye crystals start to develop their colors and combine together at up to 300 times their normal size forming meta-dyes. Surplus oxygen reacts with existing natural hair pigments to produce a slight lifting effect.

Kit According to the Teachings Herein

In some embodiments a kit according to the teachings herein comprises:

a) a first container in the form of bottle 1 (FIG. 1B) containing e.g. of 40 cc of liquid/creme permanent hair dye (cosmetic pigment included).
b) a second container in the form of bottle 2 (FIG. 1C) containing e.g. 40 cc of creme developer 50 or oxidant.
c) a 2.5 ml measuring spoon 3 (figures lB, 1C, 1D, 1E).
d) a small mixing bowl 4 (FIGS. 1D, 1E, IF).
e) An applicator in the form of make-up sponge stick 5 (FIGS. 1 F, 1 G, 2). (e.g. a brush).
f) disposable gloves.

Such a kit is suitable for approximately 16 separate applications

Method According to the Teachings Herein i. The user puts on gloves (f) (not shown in the figures).
ii. The first bottle 1 is shaken to suspend the cosmetic pigment (FIG. 1 A) and then 2.5 ml is poured from the first bottle 1 into the measuring spoon 3 (FIG. 1B), and from the measuring spoon 3 into the mixing bowl 4 (FIG. 1D).
iii. 2.5 ml is poured from the second bottle 1 into the measuring spoon 3 (FIG. 1 C), and from the measuring spoon 3 into the mixing bowl 4 (FIG. 1D);
iv. The contents of mixing bowl 4, 5 ml, are mixed well, optionally using the measuring spoon 3 to make a permanent hair dye composition 30 (FIG. 1E).
v. The end of the make-up sponge stick 20 is gently dipped into the permanent hair dye composition 30 in the mixing bowl (FIG. 1F) and applied to the at least one grey part of the subject's hair 7 (FIG. 1G) optionally with small gentle bursts.
vi. 30 minutes after the application, the hair should be washed.

In a general aspect, the hair dye composition, kit and method described herein gives users the option to dye only the visible grey roots, using permanent hair dye, which includes at least one pigment particle, also referred to as a cosmetic pigment or cosmetic color pigment. The disclosure herein is directed to use of small quantities of the hair dye composition and for the hair dye composition to be used for multiple applications. Accordingly, a subject, also referred to as a user (which can be a third party providing a service to the subject) can delay for as long as possible the need to dye the subject's entire hair, thus significantly reducing the amount of chemicals employed and time wasted.

In a preferred embodiment:

1. The addition of cosmetic color pigment.
For a bottle of 71 cc of permanent hair dye, an addition of 0.0770 cc or 1/64 of a teaspoon of cosmetic color pigment is added (US Measurement).
In tests referenced herein e.g. in Examples, any less than the specified quantity above resulted in a successful hair dye, however for certain colors the pigment particle color was not visible in the permanent hair dye composition 30 applied to the hair. Less than the specified amount resulted in dye that worked and did not come off during washing of the hair i.e. the color of the cosmetic pigment was not be observed in the hair, and this made accurate coloring more difficult.
In tests referenced herein e.g. in Examples, any more than the specified quantity above ruined the permanent hair dye with the result that the dye came off the hair completely during washing.
The quantity above (0.0770 cc or 1/64 of a teaspoon) to 71 cc of permanent hair dye component 40 (about 0.11% by volume) is the correct and safe quantity for all colors of permanent hair dyes, however for black no more than about 0.10% tested successfully (0.10% tested successfully).
The color of the color pigment chosen by the user may be visible even in the hair dye bottle. The use of cosmetic pigment during the application, allows the hair dye to be absorbed immediately onto the grey roots.
The addition of color pigment to the permanent hair dye is directed to allow the user to see the color being applied directly to the hair. This serves to enable the user to accurately apply color substantially only the necessary grey roots.
In this method of coloring, with cosmetic pigment, the user may avoid applying unnecessary quantities of hair dye solutions to unnecessary locations on the hair. This serves to reduce the amount of harmful chemicals being applied to user's hair.

2. Small Quantities
The option to use smaller quantities, 5 cc (includes permanent hair dye component 40 and developer 50) in every application of permanent hair dye composition 30 is enough to cover the visible grey roots. This reduces the need to color the entire head and may significantly reduce the amount of chemicals and time wasted dyeing hair.
The provided 2.5 cc measuring spoon 3 allows the users to use smaller quantities of permanent hair dye component 40 (2.5 cc) and developer 50 (2.5 cc), thus allowing for quicker, more efficient and safer experience.

3. One of the advantages of using smaller quantities is that it allows users multiple uses of the permanent hair dye kit, unlike the rest of the available kits in the market.

4. The two factors, one being the addition of the cosmetic pigment and the other, the division of the hair dye into smaller quantities, significantly reduces the chemical scent of the hair dye mixture.

Reduces the effect of chemicals and its harmful effects on the breathing airways.

5. Using the permanent hair dye combined with cosmetic pigment in small quantities on grey roots may delay the need to dye all the roots of the hair by at least three to four months.

6. Using this method discussed above, users may be able to dye specific spots on the hair, such as the hairlines and the side burns. The user does not have to wash their hair, he may choose to clean the colored area with a small sponge dipped in shampoo, and then following up with a small sponge dipped in water. This may save significant time for users, as they can touch up their grey roots right before leaving without having to wash their hair completely.

7. Brushes

Applicator e.g. Make-Up Sponge Stick 3

A completely different brush than any regular hair brushes in the market. One side is the handle, and the other side is a dense sponge applicator.

During the permanent hair dye application process, the tip 20 of the sponge 3 is dipped into the hair dye mixture and using small compressions the hair dye is applied to the hair. This way allows the hair dye to be applied to the grey roots directly near the scalp. The permanent hair dye composition 30 gets absorbed into the grey roots. This approach may also reduce the need to open hairlines, like other products, and makes the application much simpler.

The application in this manner is accurate, drip-free and contact-free from the skin. There is no need to use gloves, and the entire application can take less than one minute.

8. The companies in the market today offer permanent hair dye kits in quantities that are intended for use on the entire hair or half the hair and without cosmetic pigment.

9. The companies in the temporary hair dye market offer hair dye that comes off during washing of the hair.

The disclosure addresses a permanent hair dye that does not come off during washing, that may be used in convenient small quantities and that may be used for multiple applications, in that it includes at least one pigment particle in a precise relative quantity in the permanent dye component, as disclosed herein, such that the permanent dye may be seen to delineate areas of application effectively immediately after application (as though it were paint) and retention of the permanent dye in the hair cuticle after washing.

For illustration purposes:

Permanent hair dye component 40 (includes cosmetic pigment)—50 cc

Developer 50—50 cc

Total quantity—100 cc

The quantity measurements may be effected using a measuring spoon 3 of 2.5 cc.

Application may be used in the following manner:

Mixing thoroughly the permanent hair dye component 40 bottle 1 to allow the cosmetic pigment to become visible.

Pouring from the bottle 1, 2.5 cc into the measuring spoon and then into the mixing bowl.

Pouring from the developer bottle 2, 2.5 cc into the measuring spoon and then into the mixing bowl.

Mixing of the two liquids (total 5 cc) using the measuring spoon 3.

Given the total quantity of 100 cc, using the 5 cc mixture (2.5 cc of dye and 2.5 cc of developer 50) allows the user 20 uses of the product.

The disclosure of embodiments herein is different from other permanent hair dye kits in the market, which only allow for single use and forces users to use large quantity of hair dye, between 40 cc and 142 cc.

Cosmetic Pigment Powders

Cosmetic pigment powders used to test the teachings herein were purchased from TKB Trading LLC, Sandream Impact LLC, Guangzhou Yrtay fine chemicals Co. Ltd.

Description: Color group: black. Inorganic, high-purity pigment. Insoluble, but miscible in water & oils. Particle size range 0.3-5.0 micrometer. Mean particle size 2.27 micrometer. CAS: 131761-9. INCI Name: CI 77499 (iron oxide black). Applications: All kinds of color cosmetics, personal care products, soaps.

Description: Color group: brown. Inorganic, high-purity pigment. Insoluble, but miscible in water & oils. Particle size range 0.3-5.0 micrometer. Mean particle size 1.42 micrometer. CAS: 1332-37-2. INCI Name: Iron oxide blend. Applications: All kinds of color cosmetics, personal care products, soaps.

Description: Color group: red. Inorganic, high-purity pigment. Insoluble, but miscible in water & oils. Particle size range 0.3-1.0 micrometer. Mean particle size 0.56 micrometer. CAS: 1309-371. INCI Name: CI 77491 (iron oxide red). Applications:

All kinds of color cosmetics, personal care products, soaps.description: Natural shimmer pigment derived from the mineral Muscovite mica coated with iron oxides. Cosmetic-grade fineness (particle size range 10-60 um), permitted exempt color for cosmetic use. Insoluble, but miscible in liquids (sinks to bottom in thin liquids). CAS: 12001-262, 1345-25-1. INCI Name: Mica (CI 77019), iron oxide (CI 77491) cinnamon. Use: Suspends best in thick bases. Can be blended with other pigments. For external use only. Applications: All kinds of decorative cosmetics & personal care Products. Natural shimmer pigment derived front the mineral Muscovite mica coated with titanium dioxide & iron oxide. Cosmetic-grade fineness (medium particle size <15 um), permitted exempt color for cosmetic use. Insoluble, but miscible in liquids (sinks to bottom in thin liquids). CAS: 12001-26-2, 13463-67-7, 1345-25-1. INCI Name: Mica (CI 77019), titanium dioxide (CI 77891), iron oxide (CI 77491). Properties: Gives deep color with shimmering & pearlizing luminescence. Mica gold. Use: Suspends best in thick bases. Can be blended with other pigments. For external use only option: Natural shimmer pigment coated with iron oxides. Cosmetic-grade fineness (particle size range 10-60 um). Permitted exempt color for cosmetic use. Insoluble, but easily dispersible in liquids (sinks to bottom in thin liquids). CAS: 12001-26-2, 1332-37-2. INCI Name: Mica (CI 77019), iron oxide. Properties: Provides brown beige coloring with pearlizing luminescence. Mica walnut brown. Use: Suspends best in thick bases. Can be blended with other pigments. For external use only. Applications: All kinds of decorative cosmetics & personal care products.

Model: YT4001, color: Bronze, particle diameter ÷10-60 mih. Characteristic description: Metallic effect pearl pigment has glitter bronze luster, high hiding power. Model: SW6500, color: Crystal bronze, particle diameter: 10-60 μm.

Characteristic description: Antique bronze metallic luster, more sparkle than the metallic effect pearl pigment.

Alchemique Amber, Color: Amber. Composition: Aluminum Powder, Silica, Iron Oxides. Particle Size: 30-60 μm. Application: Eye, Face, Nail and Personal Care worldwide Aynmira Shimmer ROY8598, Color: Color Travel. Composition: Synthetic Fluorphlogopite, Titanium Dioxide, Tin Oxide, Silica, Iron Oxides. Particle Size: 20-80 μm/Application: Eye, Lip, Face, Nail and Personal Care worldwide.

Majestic Mango, Color: Mango. Composition: Mica, Yellow 5 Lake. Particle Size: 10-60 μm. Application: Eye, Lip, Face, Nail and Personal Care worldwide* Conditionally approved for eye applications in selected countries in Asia

EXAMPLES

Permanent Hair Dye Kits

Prior art permanent hair dye kits were purchased from regular commercial stores in Vancouver, Canada. Permanent hair dyes are intended for coloring grey roots. These hair dyes do not come off during or after washing. All permanent hair dye kits are single-use only.

Kit #1: Wella ColorCharm® liquid haircolor 3N dark natural brown (coloring solution including ammonia) with Wella cream developer (developer for use with ColorCharm®, including hydrogen peroxide).

Kit #2: Wella Koleston® 4/77 (velvety brown) kit including coloring solution including ethanol amine and developer including hydrogen peroxide.

Kit #4: L'Oreal® (Golden Copper) ColorSpa Moisture Actif® including a colorant with ethanolamine and a developer including hydrogen peroxide.

Kit #5: Garnier® Olia® (5.3 Golden Brown) including a colorant with ethanolamine and a viscous cream developer including hydrogen peroxide.

Kit #6; Revlon® ColorSilk® (burgundy) including a colorant with ethanolamine and a developer including hydrogen peroxide.

Kit #7: SchwarzKopf color Ultime (1.4 sapphire black) including developer.

Kit #8: Revlon COLORSILK—free Ammonia.

Kit #9: Revlon—COLORSILK-30 Dark Brown—Ammonia free.

Kit #10: GARNIER-700 Dark Natural Blonde—free Ammonia.

Kit #11: LOreal-CASTING—600 Light Brown—No Ammonia.

Kit #12: COLOR BRILLIANCE—Ion—305478—Blue Black PPD Free and free.

Kit #13: CoSaMo-Love Your Color—Light Ash Brown—PPD Free.

Cosmetic Pigment Powders

Cosmetic pigment powders used to test the teachings herein were purchased from TKB Trading LLC:

a. Black Oxide Pigment (black iron oxide, CAS No. 1317-61-9);

b. Antique Copper (mica (CAS No. 12001-26-2), titanium dioxide (CAS No. 13463-67-7), red iron oxide (CAS No. 1309-37-1), black iron oxide (CAS No. 1317-61-9)); and c. Colorona Russet, (mica (CAS No. 12001-26-2), titanium dioxide (CAS No. 13463-67-7), red iron oxide (CAS No. 1309-37-1)).

Additional pigment powders used were:

d. 1-pigment powders;

e. 30-color eyeshadow palette by YeSurprise;

f. Sephora Color Anthology eyeshadow;

g. commercial eye shadow; and h. Chanel ombré eye shadow palette

Although the particle sizes were not measured, it is believed that the mean particle size of all the cosmetic pigment powders was between 10 micrometers and 100 micrometers, with substantially no particles larger than 150 micrometers.

General Method

In some general embodiments, the permanent dye component comprises 0.05% to 0.13% by volume of the at least one pigment particle, optionally 0.09% to 0.12% by volume of the at least one pigment particle.

The experiments were conducted on women ranging from the ages of 35 to 72 years old.

A prior art hair coloring composition was made from any one of Kits #1 to #13 by combining appropriate amounts of the developer and corresponding permanent hair dye solution.

The addition of cosmetic pigment was added to both liquid-form permanent hair dye and to creme-form permanent hair dye. Addition of 0.0770 cc or 1/64 tsp (US measurements) of cosmetic pigment is added to a bottle of 71 cc of liquid (or créme) permanent hair dye. For the liquid permanent hair dye with the cosmetic pigment, the user must shake the liquid bottle well before use in order to combine the sunk pigment with the rest of the composition. For creme-form permanent hair dye the cosmetic pigment remains in the composition without any changes, no shaking necessary.

Pouring from the permanent hair dye component 40 bottle 1 as illustrated in FIG. 1B (which optionally includes the cosmetic pigment) into a measuring spoon 3 of 2.5 cc and then pouring it into the mixing bowl 4 as illustrated in FIG. 1D. Subsequently, pouring 2.5 cc of the developer into the measuring spoon 3 as illustrated in FIG. 1C and then into the mixing bowl 4 as illustrated in FIG. 1D. Mixing the two well using the measuring spoon 3 as illustrated in FIG. 1E. Application of the thus-made hair coloring composition according to the teachings herein exemplified in FIG. 1G is done using a make-up sponge stick 5 or high-density applicator, which has a handle 10 on one side and a dense foam tip 20 at the other end. Only the very tip of 20 of the sponge stick or applicator 5 was gently dipped into the hair coloring composition in the bowl and then is applied by dabbing the visible grey hairs (at the parts and sideburns). The small dabs allow the hair coloring composition to be applied evenly and more thoroughly to the roots of the grey hair, close to the scalp. Each application is optionally in the quantity of 5 cc and includes hair dye, developer and cosmetic pigment without any chemical scent. All the hair to be colored of given subject was colored within approximately 5 minutes of making the hair composition according to the teachings herein.

Each 5 ml batch of hair-coloring composition according to the teachings herein was sufficient for coloring all the visible grey roots of a subject's head, Thus, a single prior art kit for making 142 ml of prior art hair coloring composition was enough for making 28 separate 5 ml batches of hair coloring composition according to the teachings herein.

In some instances, when the amount of cosmetic pigment powder that was added was less than 1/64 tsp, successful hair dyeing was achieved but the color was not immediately visible when applied to the hair.

Amounts of cosmetic pigment powder greater than about 1/64 tsp have tested to ruin the prior art hair coloring composition thus resulting in fading of the dyed hair after washing.

When coloring of a subject's hair was completed, the subject waited between 20 and 35 minutes.

Typically, after 20 to 35 minutes of the application the user can choose to wash their hair in the shower or clean it with a sponge dipped in shampoo followed by a sponge dipped in water.

Hair colored according to the teachings herein was monitored during 18 months period. Hair was washed normally (typically at least one shower a day) using standard shampoo and conditioner).

No fading of the color resulting from application of the composition was observed and the only grey color was of new hair growth emerging from the scalp.

Hair care professionals who were asked to cut, style and trim the hair remarked that the hair had regained a youthful and vibrant appearance. Without wishing to be held to any one theory, it is currently believed that since subjects no longer applied standard hair coloring compositions to their hair, the hair remained undamaged along its length.

Unless otherwise defined, all technical and scientific terms used herein have the same meaning as commonly understood by one of ordinary skill in the art to which the invention pertains. In case of conflict, the specification, including definitions, will take precedence.

As used herein, the terms "comprising", "including", "having" and grammatical variants thereof are to be taken as specifying the stated features, integers, steps or components but do not preclude the addition of one or more additional features, integers, steps, components or groups thereof. These terms encompass the terms "consisting of" and "consisting essentially of".

As used herein, the indefinite articles "a" and "an" mean "at least one" or "one or more" unless the context clearly dictates otherwise.

As used herein, when a numerical value is preceded by the term "about", the term "about" is intended to indicate +/−10%.

As used herein, a phrase in the form "A and/or B" means a selection from the group consisting of (A), (B) or (A and B). As used herein, a phrase in the form "at least one of A, B and C" means a selection from the group consisting of (A), (B), (C), (A and B), (A and C), (B and C) or (A and B and C).

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Citation or identification of any reference in this application shall not be construed as an admission that such reference is available as prior art to the invention.

Section headings are used herein to ease understanding of the specification and should not be construed as necessarily limiting.

What is claimed is:

1. A hair dye composition comprising a predetermined amount of a permanent hair dye component of a type that is mixed with a predetermined developer component in a predetermined ratio by volume to prepare a permanent hair dye composition that is applied to a subject's hair and maintained in the subject's hair for at least a period of a predetermined minimum duration before washing the subject's hair, the permanent dye component comprising at least one coupler compound in an amount effective to attain a selected hair color of the subject's hair, the selected color arranged to match a predetermined color selected by or for the subject such that the permanent hair dye composition may be used to touch-up at least one grey part of the subject's hair in new growth areas to match at least one non-grey part previously dyed to attain the predetermined color, the permanent hair dye component comprising 0.05% to about 0.11% by volume of at least one pigment particle that is evenly distributable within the permanent hair dye composition, the at least one pigment particle being of a visible color such that application of the permanent hair dye composition to a surface of the at least one grey part of the subject's hair may be observed to have the visible color of a plurality of the at least one pigment particle contemporaneously with application to the surface;

wherein the visible color of the at least one pigment particle matches the predetermined color; and wherein the particle size of 99% by weight of the at least one pigment particle does not exceed 150 microns.

2. The composition of claim 1, wherein the permanent dye component comprises 0.09% to 0.11% by volume of the at least one pigment particle.

3. The composition of claim 1, wherein the percentage by volume of the at least one pigment particle in the permanent dye component does not exceed 0.11%, provided that wherein the selected color is black, the percentage by volume of the at least one pigment particle in the permanent dye component does not exceed 0.10%.

4. The composition of claim 1, wherein the percentage by volume of the at least one pigment particle in the permanent dye component is 0.11%.

5. The composition of claim 1, wherein the permanent hair dye component comprises a primary intermediate compound, a hair-cuticle opening agent and at least one coupler compound.

6. The composition of claim 1, wherein the predetermined developer component comprises an oxidizing agent selected from the group comprising hydrogen peroxide.

7. The composition of claim 1, wherein the particle size of at least 99% by weight of the at least one pigment particle is between 10 and 100 microns.

8. The composition of claim 1, in a container comprising a reusable closure device and a predetermined volume of the permanent hair dye component in a liquid form, the predetermined volume being sufficient for multiple touch-up applications of the hair dye composition to new growth of a non-grey part of the subject's hair of the predetermined color, the container provided with instructions for shaking the container before use.

9. The composition of claim 1, in a container comprising a reusable closure device and a predetermined volume of the permanent hair dye component in a cream form, the predetermined volume sufficient for multiple touch-up applications of the hair dye composition to new growth of a non-grey part of the subject's hair of the predetermined color.

10. The composition of claim 8, wherein the container is provided with instructions in at least one language for mixing a specific volume of the predetermined amount of the permanent hair dye component with a predetermined amount of the predetermined developer component corresponding to the predetermined ratio by volume.

11. A kit comprising a composition as claimed in claim 1, in a container.

12. A kit as claimed in claim 11, further comprising a second container with a reusable closure, the second container comprising at least a volume of the predetermined developer component sufficient to make the permanent hair dye composition in an amount sufficient for a selected number of applications.

13. A kit as claimed in claim 11, further comprising an applicator, the applicator comprising at least one surface with a surface area configured for selectively applying the permanent hair dye composition to at least one region of subject's hair, said at least one region comprising a grey part of the subject's hair including a region proximal to the roots of the subject's hair.

14. A kit as claimed in claim 13, wherein the applicator has a flat edge or pointed tip.

15. A kit as claimed in claim 13, wherein the applicator is a washable sponge applicator.

16. A kit as claimed in claim 11, wherein the instructions further comprise instructions for using the kit including applying the permanent hair dye composition to the subject's hair with a suitable applicator, allowing the permanent hair dye composition to remain in subject's hair for at least the period and washing the hair after this period.

17. A kit as claimed in claim 11, further comprising a mixing bowl of a volume sufficient to mix an amount of the permanent hair dye component at least sufficient for one application with an amount of developer in the predetermined ratio by volume.

18. A kit as claimed in claim 13, further comprising gloves.

19. A kit as claimed in claim 8, further comprising a measuring spoon suitable for measuring a volume of approximately 2.5 milliliters.

20. A hair dye composition comprising a predetermined amount of a permanent hair dye component of a type that is mixed with a predetermined developer component in a predetermined ratio by volume to prepare a permanent hair dye composition that is applied to a subject's hair and maintained in the subject's hair for at least a period of a predetermined minimum duration before washing the subject's hair, the permanent dye component comprising at least one coupler compound in an amount effective to attain a selected hair color of the subject's hair, the selected color arranged to match a predetermined color selected by or for the subject such that the permanent hair dye composition may be used to touch-up at least one grey part of the subject's hair in new growth areas to match at least one non-grey part previously dyed to attain the predetermined color, the permanent hair dye component comprising 0.05% to about 0.11% by volume of at least one pigment particle that is evenly distributable within the permanent hair dye composition, the at least one pigment particle being of a visible color such that application of the permanent hair dye composition to a surface of the at least one grey part of the subject's hair may be observed to have the visible color of a plurality of the at least one pigment particle contemporaneously with application to the surface;

wherein the composition is in a container comprising a reusable closure device and a predetermined volume of the permanent hair dye component in a liquid form, the predetermined volume being sufficient for multiple touch-up applications of the hair dye composition to new growth of a non-grey part of the subject's hair of the predetermined color, the container provided with instructions for shaking the container before use;

wherein the container is provided with instructions in at least one language for mixing a specific volume of the predetermined amount of the permanent hair dye component with a predetermined amount of the predetermined developer component corresponding to the predetermined ratio by volume; and wherein the specific volume corresponds to a defined period of new growth commencing from a previous application of a permanent hair dye composition of the predetermined color that covered at least the roots of the subject's hair, and wherein the specific volume is identified in the instructions as a recommended amount for a single application to the grey part of the subject's hair after the defined period of new growth.

21. The composition of claim 20, wherein defined period of new growth is 2 to 3 weeks and wherein the specific volume is approximately 2.5 milliliters.

22. A method for touching up a grey new growth area of a subject's hair having a non-grey part dyed with a permanent dye of a predetermined color, the method comprising the following steps carried out by or for the subject:
 a) shaking The permanent dye component in a predetermined manner;
 b) mixing a permanent dye component with a predetermined developer component in a predetermined ratio by volume to prepare a permanent hair dye composition comprising at least one coupler compound effective to attain a selected hair color that matches the predetermined color;
 c) applying the permanent hair dye composition to grey parts of the subject's hair;
 d) allowing the permanent hair dye composition to remain in the subject's hair for at least a period of predetermined minimum duration;
 e) washing the permanent hair dye composition out of the subject's hair;
 the permanent hair dye component comprising 0.05 to about 0.11% by volume of pigment particles of a visible color such that application of the permanent hair dye composition to a surface of the grey part of the subject's hair may be observed to have the visible color of the pigment particle contemporaneously with application to the surface, the predetermined manner sufficient to evenly suspend the pigment particle in the permanent hair dye component;
 wherein the visible color of the at least one pigment particle matches the predetermined color; and
 wherein the particle size of 99% by weight of the at least one pigment particle does not exceed 150 microns.

23. The composition of claim 5, wherein the primary intermediate compound comprises an aromatic amine that forms an imine on oxidation, the aromatic amine being selected from the group consisting of 1,4-diaminobenzene, diaminotoluene, p-aminophenol, derivatives thereof and combinations thereof.

24. The composition of claim 5, wherein the hair-cuticle opening agent is selected from the group consisting of ammonia, ethanolamine, diethanolamine, sodium carbonate and derivatives thereof and combinations thereof.

25. The composition of claim 5, wherein t at least one coupler compound is selected from the group consisting of a phenol, naphthol, resorcinol, 4-chlororesorcinol, benzodioxole, 1,4-diaminobenzene, 2,5-diaminotoluene, p-aminophenol, and derivatives thereof and combinations thereof.

* * * * *